US010285852B2

(12) United States Patent
Rotenstreich

(10) Patent No.: US 10,285,852 B2
(45) Date of Patent: May 14, 2019

(54) SUBRETINAL DELIVERY OF THERAPEUTIC COMPOSITIONS

(75) Inventor: Ygal Rotenstreich, Kfar Bilu (IL)

(73) Assignee: TEL HASHOMER MEDICAL RESEARCH INFRASTRUCTURE AND SERVICES LTD., THE CHAIM SHEBA MEDICAL CENTER, Ramat Gan (IL)

( * ) Notice: Subject to any disclaimer, the term of this patent is extended or adjusted under 35 U.S.C. 154(b) by 1139 days.

(21) Appl. No.: 13/988,570

(22) PCT Filed: Nov. 28, 2011

(86) PCT No.: PCT/IB2011/055335
§ 371 (c)(1),
(2), (4) Date: May 21, 2013

(87) PCT Pub. No.: WO2012/073180
PCT Pub. Date: Jun. 7, 2012

(65) Prior Publication Data
US 2013/0253416 A1    Sep. 26, 2013

Related U.S. Application Data

(60) Provisional application No. 61/419,160, filed on Dec. 2, 2010.

(51) Int. Cl.
*A61F 9/00* (2006.01)
*A61B 17/34* (2006.01)
(Continued)

(52) U.S. Cl.
CPC .... *A61F 9/0017* (2013.01); *A61B 2017/3405* (2013.01); *A61F 9/0133* (2013.01); *A61M 5/3287* (2013.01)

(58) Field of Classification Search
CPC .......... A61B 2017/3405; A61F 9/0017; A61F 9/0133; A61F 2009/00865; A61M 5/3287; A61M 2210/0612
See application file for complete search history.

(56) References Cited

U.S. PATENT DOCUMENTS 4,324,044 A * 4/1982 Shahinian, Jr. .. A61B 17/32093
30/294
5,273,530 A * 12/1993 del Cerro ............ A61F 9/00736
604/117
(Continued)

FOREIGN PATENT DOCUMENTS

WO    2000/007530    2/2000
WO    2008/084063    7/2008
WO    2012/073180 A1    6/2012

OTHER PUBLICATIONS http://www.retinalphysician.com/articleviewer.aspx?articleID=103195; Steps for a safe intravitreal injection technique; pp. 1-5; published Jul. 1, 2009.*

(Continued)

*Primary Examiner* — Jenna Zhang
(74) *Attorney, Agent, or Firm* — The Law Office of Joseph L. Felber

(57) ABSTRACT

Disclosed are methods of subretinal delivery of therapeutic compositions to the eye of a mammal. Also disclosed are devices useful for the subretinal delivery of therapeutic compositions to the eye of a mammal.

23 Claims, 10 Drawing Sheets

(51) Int. Cl.
*A61F 9/013* (2006.01)
*A61M 5/32* (2006.01)

(56) References Cited

U.S. PATENT DOCUMENTS

| | | | | |
|---|---|---|---|---|
| 5,312,413 | A * | 5/1994 | Eaton | A61B 17/320016 30/151 |
| 5,360,425 | A | 11/1994 | Cho | |
| 5,409,457 | A * | 4/1995 | del Cerro | A61F 9/00736 604/117 |
| 5,411,510 | A * | 5/1995 | Fugo | A61B 17/3211 128/898 |
| 5,545,153 | A | 8/1996 | Grinblat et al. | |
| 5,941,250 | A * | 8/1999 | Aramant | A61F 9/00727 128/898 |
| 6,309,374 | B1 * | 10/2001 | Hecker | A61F 9/007 604/117 |
| 6,378,526 | B1 * | 4/2002 | Bowman | A61K 9/0048 128/898 |
| 7,824,372 | B1 * | 11/2010 | Kurup | A61F 9/0017 604/116 |
| 8,425,473 | B2 | 4/2013 | Ho et al. | |
| 8,808,242 | B2 | 8/2014 | Paques et al. | |
| 2001/0008961 | A1 * | 7/2001 | Hecker | A61F 9/007 604/117 |
| 2001/0029363 | A1 | 10/2001 | Lin | |
| 2002/0133184 | A1 * | 9/2002 | LoRusso | A61F 9/00727 606/167 |
| 2002/0198511 | A1 * | 12/2002 | Varner | A61F 9/0017 604/521 |
| 2003/0097117 | A1 * | 5/2003 | Buono | A61F 9/0017 604/521 |
| 2003/0171722 | A1 * | 9/2003 | Paques | A61F 9/0017 604/264 |
| 2004/0208847 | A1 * | 10/2004 | Rolling | A61K 48/0075 424/93.2 |
| 2005/0203542 | A1 * | 9/2005 | Weber | A61F 2/167 606/107 |
| 2007/0202186 | A1 | 8/2007 | Yamamoto et al. | |
| 2008/0058704 | A1 | 3/2008 | Hee et al. | |
| 2008/0082078 | A1 * | 4/2008 | Berlin | A61F 9/00781 604/521 |
| 2014/0107566 | A1 | 4/2014 | Prausnitz et al. | |

OTHER PUBLICATIONS

S Wongpichedchai, J J Weiter, P Weber, C K Dorey; Comparison of external and internal approaches for transplantation of autologous retinal pigment epithelium. Invest Ophthalmol. Vis. Sci. 1992; 33(12):3341-3352.*

Eye Anatomy and Aging Eyes. Date of Aug. 17, 2010. Eye Anatomy—Vision is Changing for the Baby Boomer Generation. Accessed on Sep. 14, 2017. https://web.archive.org/web/20100817164213/http://www.healthyagingforwomenbabyboomers.com/eyeanatomy.html.*

Wongpichedchai et al. Comparison of external and internal approaches for transplantation of autologous retinal pigment epithelium. Invest Ophthalmol. Vis. Sci. 1992; 33(12: 3341-3352.*

Eye Anatomy and Aging Eyes. Date of Aug. 17, 2010. Eye Anatomy—Vision is Chaning for the Baby Boomer Generation. Accessed on Sep. 14, 2017. https://web.archive.org/web/20100817164213/http://www.healthyagingforwomenbabyboomers.com/eyeanatomy.html.*

Wongpichedchai et al. Comparison of external and internal approaches for transplantation of autologous retinal pigment epithelium. Invest Ophthalmol. Vis. Sci. 1992; 33(12): 3341-3352. (Year: 1992).*

Patel et al., "Suprachoroidal Drug Delivery to the Back of the Eye Using Hollow Microneedles," Pharm Res (2011) 28:166-176, Sep. 21, 2010, Springer Science+Business Media, LLC 2010.

Patel et al., "Targeted Administration into the Suprachoroidal Space Using a Microneedle for Drug Delivery to the Posterior Segment of the Eye," Physiology and Pharmacology, Investigative Ophthalmology & Visual Science, Jul. 2012, vol. 53, No. 8, The Association for Research in Vision and Ophthalmology, Inc.

Tetz et al., "Safety of Submacular Suprachoroidal Drug Administration via a Microcatheter: Retrospective Analysis of European Treatment Results," Ophthalmologica 2012;227:183-189, S. Karger AG, Basel.

International Search Report and Written Opinion of PCT/IB2011/055335.

Francis et al., "Subretinal Transplantation of Forebrain Progenitor Cells in Nonhuman Primates: Survival and Intact Retinal Function," Invest Ophthalmol Vis Sci. Jul. 2009; 50(7): 3425-3431. doi:10.1167/iovs.08-2908.

Canola et al, "Retinal Stem Cells Transplanted into Models of Late Stages of Retinitis Pigmentosa Preferentially Adopt a Glial or a Retinal Ganglion Cell Fate," Investigative Ophthalmology & Visual Science, Jan. 2007, vol. 48, No. 1, pp. 446-454.

Wang et al., "Transplantation of Reprogrammed Embryonic Stem Cells Improves Visual Function in a Mouse Model for Retinitis Pigmentosa," Transplantation • vol. 89, No. 8, Apr. 27, 2010, pp. 911-919.

Hynes et al., "A tissue-engineered approach towards retinal repair: Scaffolds for cell transplantation to the subretinal space," Graefes Arch Clin Exp Ophthalmol DOI 10.1007/s00417-009-1263-7, published online Feb. 19, 2010.

Lamba et al., "Transplantation of human embryonic stem cells derived photoreceptors restores some visual function in Crx deficient mice," Cell Stem Cell. Jan. 9, 2009; 4(1): 73-79. doi:10.1016/j.stem.2008.10.015.

* cited by examiner

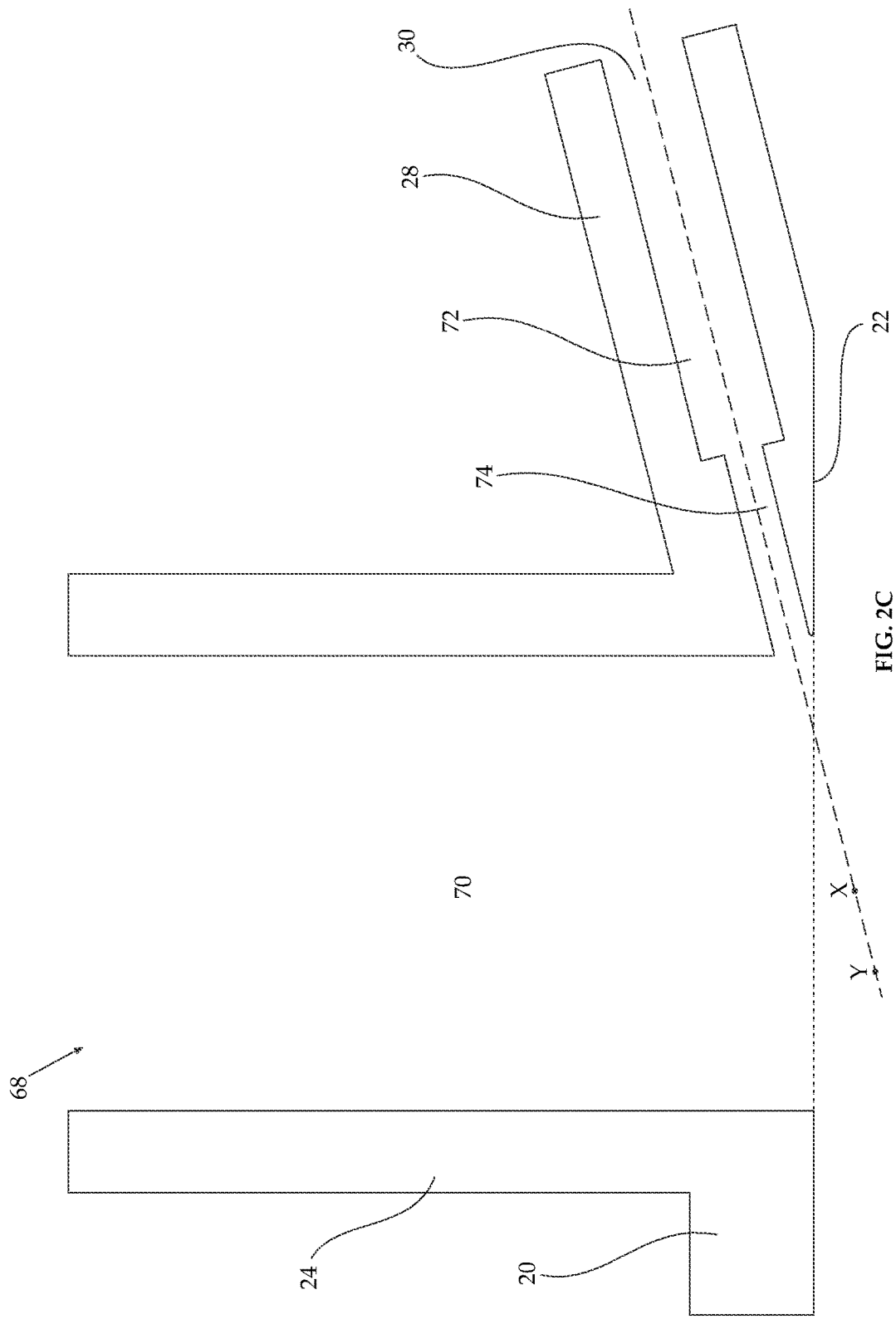

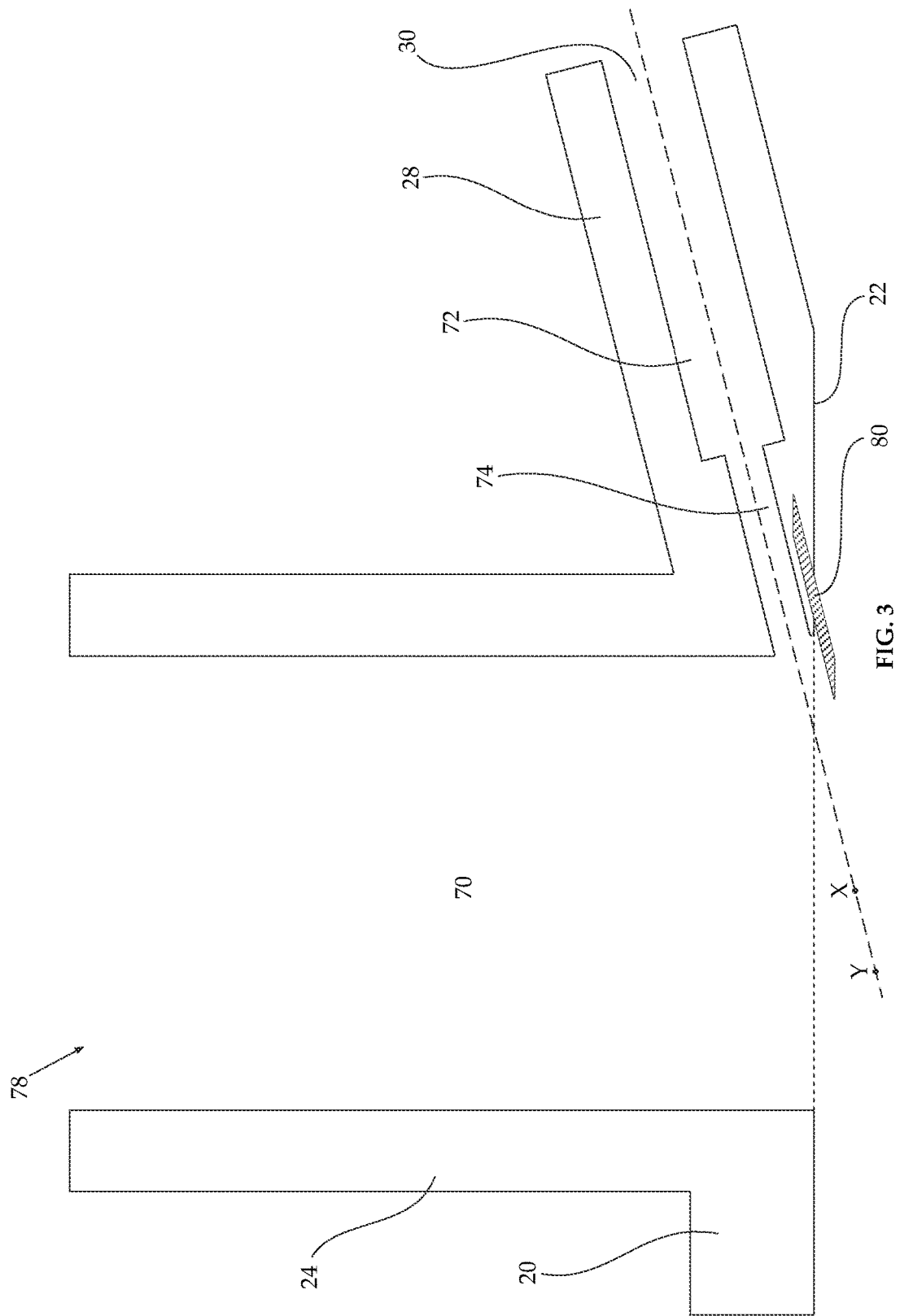

SUBRETINAL DELIVERY OF THERAPEUTIC COMPOSITIONS

RELATED APPLICATION

This Application is a national phase of, and claims priority from, PCT Application No. PCT/IB2011/055335, filed on Nov. 28, 2011, which claims priority from U.S. Provisional Application No. 61/419,160, filed Dec. 2, 2010, which is hereby incorporated by reference as if fully set forth herein.

FIELD AND BACKGROUND OF THE INVENTION

The invention, in some embodiments, relates to the field of ophthalmic surgery.

The eye comprises three main layers: an outer layer of tough, white, opaque, membrane known as the sclera; a middle layer known as the choroid, the front of which is the iris; and an inner layer, known as the retina, which lines the back two-thirds of the eye. The retina consists of two sublayers: the sensory retina, which contains photoreceptor cells (rods and cones) which convert light images into electrochemical signals and the retinal pigment epithelium (RPE). Cells of the RPE absorb excess light and transport oxygen, nutrients, and cellular waste between the photoreceptors and the choroid. The RPE is separated from the photoreceptor outer segments by the subretinal space.

The macula is an oval-shaped highly pigmented yellow spot near the center of the retina. Near the center of the macula is the fovea, a small pit that contains the largest concentration of cone cells in the eye and is responsible for central vision, and also contains the parafovea and perifovea.

Neuroretinal degenerative diseases such as retinitis pigmentosa and age-related macular degeneration (AMD), which involve death of cells in the RPE layer, are the major causes of blindness in the Western world. Such disorders are the consequence of various intrinsic and extrinsic factors and may result in the complete loss of visual function as a consequence of photoreceptor degeneration [Invest Opthalmol Vis Sci 48(1): 446-454 (2007)].

AMD is a progressive disease which primarily affects the macula. The risk for developing macular degeneration increases with age and is in excess of 30% by age 75. Other risk factors include a family history of the disease, cigarette smoking, excessive sunlight exposure, hypertension and cardiovascular disease. AMD is categorized as early AMD, dry AMD or wet AMD. The majority of AMD sufferers have early AMD, associated with minimal visual loss, which may progress to dry (atrophic) AMD or the more serious wet (exudative) AMD may develop.

In early AMD, the transport of nutrients and waste by the RPE slows down, so that waste accumulates under the retina forming yellowish deposits called drusen.

Dry macular degeneration is a slowly progressive condition characterized by the accumulation of drusen under the retina, with some visual loss. With increasing drusen accumulation, the overlying photoreceptors become damaged and atrophy.

In wet macular degeneration, new blood vessels grow underneath the retina in a process called choroidal neovascularization. These blood vessels may leak blood or fluid under the retina, causing the retinal surface to become uneven, so that portions of the visual field are distorted. As the condition progresses, blind spots may appear.

AMD affects approximately 8 million Americans, and its incidence is expected to double by 2020 [Transplantation 89(8): 911-919 (2010)]. Hence, AMD makes up a significant proportion of neurodegenerative diseases that severely impair activities of daily living.

Retinitis pigmentosa is a group of inherited diseases associated with abnormalities of the photoreceptors or the RPE, and characterized by progressive peripheral vision loss and night vision difficulties that can lead to central vision loss.

It has been suggested that cell-based therapy, wherein cells such as progenitor cells or stem cells, are engrafted into the subretinal space, may prove efficacious for several currently untreatable conditions involving the RPE layer, including retinitis pigmentosa, and AMD [Invest Opthalmol Vis Sci 50(7): 3425-3431 (2009)]. Cell transplantation into the human retina has the potential to restore lost vision and to provide treatment of advanced stages of retinal degeneration with significant RPE loss.

Subretinal injection is commonly used clinically for the delivery of therapeutic compositions to the subretinal space. An efficient delivery method is expected to achieve a uniform distribution of injected composition throughout the subretinal space including to the macula.

Known methods of subretinal delivery include those in which a sharp injection device, e.g., a syringe having a sharpened hollow needle, is used to penetrate the sclera from outside the eye to the subretinal space where the composition is injected. A major drawback of this method is that the composition remains localized in the subretinal space near the injection site and does not reach the macula.

Other methods which are intended to deliver compositions to the macula include inserting a thin flexible catheter from an incision site in the front sclera, through the subretinal space from the incision site until the distal end of the catheter is near the macula to deliver the composition near the macula. Disadvantages of such methods include the risk of severe detachment of the retina from the sclera caused by the catheter, and risk of damaging the retina during the procedure.

In another known method, an incision is made in the frontal part of the sclera and a sharp rigid cannula is inserted into an incision in the eye, across the eye, through the vitreous humor chamber to pierce the sensory retina across the incision site to enter the subretinal space near the macula where the composition is delivered. In addition to the fact that the injected compound remains localized in the subretinal space near the injection site, other drawbacks of this vitrectomy-like surgery include increased chance of cataract development, high ocular pressure and bleeding in the eye. Moreover, the need for repeated injections may require several incisions in the frontal part of the sclera.

SUMMARY OF THE INVENTION

Some embodiments of the invention relate to methods and devices for subretinal delivery of therapeutic compositions that, in some embodiments, allow a more homogeneous distribution of the injected composition with a reduced incidence of retinal detachment than some methods known in the art.

According to an aspect of some embodiments of the invention, there is provided a method for subretinal delivery of a therapeutic composition to the eye of a subject (human or non-human mammal) in need thereof, the method comprising:

a) inserting a piercer into an eye to make an incision through the sclera (and the retinal pigment epithelium) to the subretinal space of the eye;

b) subsequent to 'a', inserting an injector into the incision; and c) injecting a therapeutic composition through the incision to the subretinal space of the eye using the injector.

According to an aspect of some embodiments of the invention there is also provided a device and/or a kit suitable for subretinal delivery of a composition, comprising:

a guide configured to make contact with a surface of an eye of a subject (human or non-human mammal);

a piercer configured for making an incision through the sclera (and retinal pigment epithelium) to the subretinal space of the eye, when inserted through the guide; and an injector, for subretinal injection of a therapeutic composition when the injector is inserted through the guide into an incision made by the piercer.

According to an aspect of some embodiments of the invention there is also provided a guide suitable for assisting in the subretinal delivery of a composition, the guide configured to guide a piercer to make an incision through a sclera of the desired dimensions and angle to the subretinal space of an eye, and the guide also configured to guide an injector into the incision (in some embodiments, substantially coaxially to the incision) in order to properly inject the composition into the subretinal space.

Unless otherwise defined, all technical and scientific terms used herein have the same meaning as commonly understood by one of ordinary skill in the art to which the invention pertains. In case of conflict, the specification, including definitions, will control.

In addition, the materials, methods, and examples are illustrative only and not intended to be limiting.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetic symptoms of a condition or substantially preventing the appearance of clinical or aesthetic symptoms of a condition.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

The term "pharmaceutically effective amount" denotes that dose of an active ingredient or a composition comprising the active ingredient that will provide the therapeutic effect for which the active ingredient is indicated.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIGS. 2A-2C are schematic depictions of an embodiment of a guide of device as described herein, in perspective (2A), bottom view (2B) and side cross section (2C);

FIG. 3 is a schematic depiction of a guide of a device as described herein in side cross section.

DESCRIPTION OF SOME EMBODIMENTS OF THE INVENTION

Figure 1A:
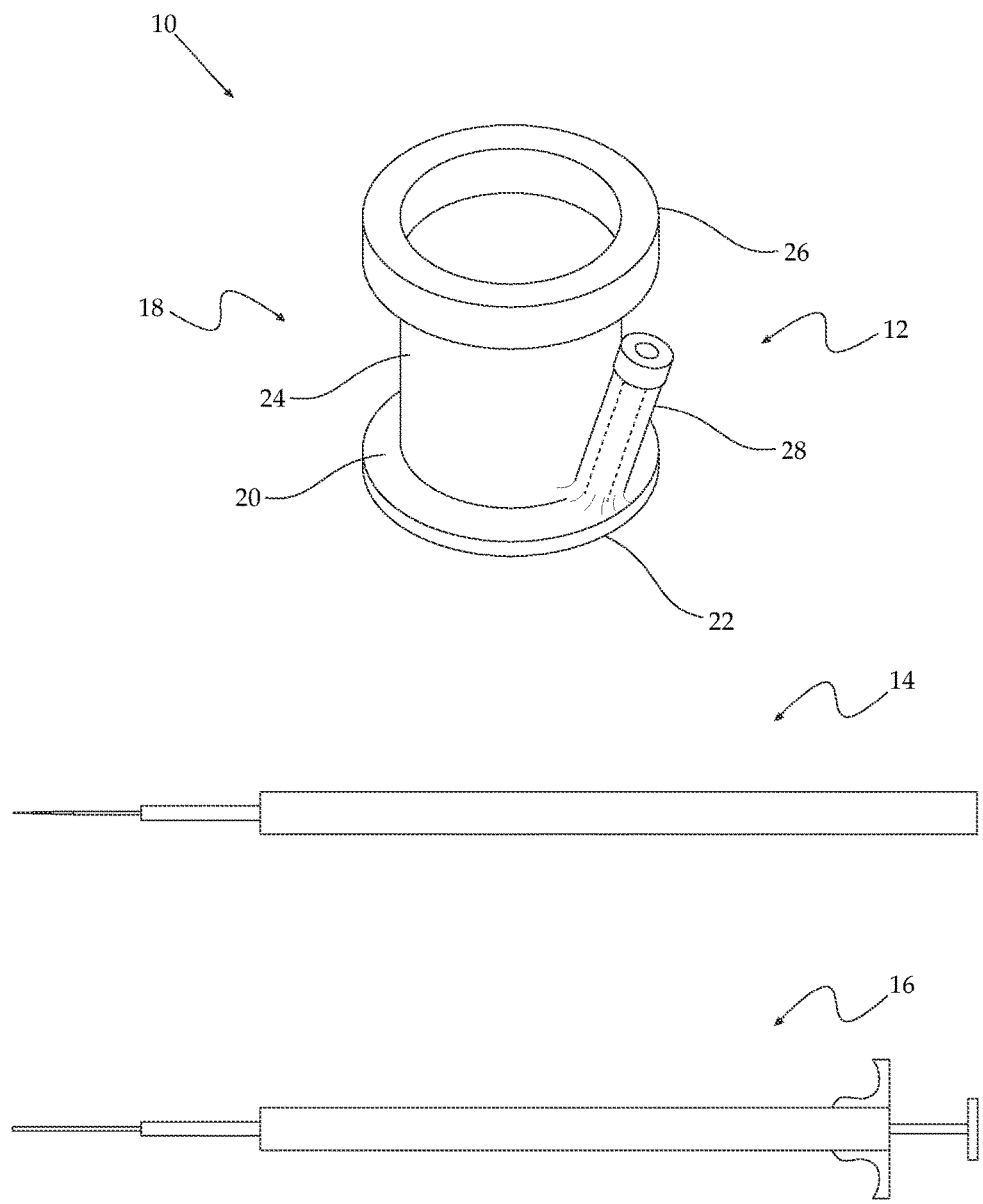
FIG. 1A is a schematic depiction of an embodiment of a device as described herein.

The invention, in some embodiments thereof, relates to methods for subretinal delivery of fluid therapeutic compositions as well as subretinal delivery devices useful for the delivery of fluid therapeutic compositions to the subretinal space of an eye.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

According to an aspect of some embodiments of the invention, there is provided a method for subretinal delivery of a therapeutic composition to the eye of a subject (human or non-human mammal) in need thereof, the method comprising:

a) inserting a piercer into an eye to make an incision through the sclera (and retinal pigment epithelium) to the subretinal space of the eye;

b) subsequent to 'a', inserting an injector into the incision; and c) injecting a therapeutic composition through the incision to the subretinal space of the eye using the injector.

In some embodiments, the piercer is inserted to a depth so that the incision passes through the sclera, choroid and retinal pigment epithelium to the subretinal space of the eye. Generally, when the incision reaches the subretinal space, blood is observed coming from the incision, e.g., around the piercer. In some embodiments, insertion of the piercer into the eye is stopped when blood is observed coming from the incision, indicating that the piercer has reached the subretinal space.

Subsequently, the injector is inserted into the incision and while inside the incision, the therapeutic composition is injected into the subretinal space using the injector.

In some embodiments, the distal tip of the injector is advanced to the end of the incision to inject the therapeutic composition directly into the subretinal space, that is to say, the distal tip of the injector is inserted into the subretinal space prior to the injection. In some embodiments, the distal tip of the injector is advanced only partially into the incision, for example, so that the distal tip of the injector is located inside the sclera or inside the retinal pigment epithelium when the therapeutic composition is injected.

In some embodiments, the injector is inserted through the incision while the piercer is still in the incision. In some embodiments, the piercer is withdrawn from the incision prior to inserting the injector through the incision.

Although not wishing to be held to any one theory, it is currently believed that first making an incision through the sclera to the subretinal space and subsequently inserting an injector through the incision to inject a composition allows, in some embodiments, a homogenous distribution of injected composition in the subretinal space. It is currently believed, that the two steps, piercing the sclera to make a passage through the sclera followed by composition-injection, allow the sclera to seal around the portion of the injector that is found in the incision in a way that leads to a distribution of fluid pressure in the eye that leads to a substantially homogenous distribution of an injected composition in the subretinal space, in some embodiments including to the macula.

In some embodiments, the incision is a slit, that is to say has a width dimension substantially greater than height dimension. In some embodiments, a slit incision provides a better seal around the portion of the injector that is found in the incision. In some embodiments, the wound produced by a slit incision heals more easily than a puncture or other incision. In some embodiments, the width of the incision is not less than 150% and even not less than 200% of the height of the incision.

In some embodiments, the injector is an elongated injector having a distal end and a distal tip, the distal tip having cross-sectional dimensions not smaller than a distal end of the incision. In some embodiments, the distal tip of the injector has cross-sectional dimensions greater than of a distal end of the incision. For example, in some embodiments, the piercer comprises a blade having a pointed shape (e.g., triangular, leaf-shaped). The distal end of the incision (made by the narrow point of the blade, for example to the subretinal space) has a small cross-section while the more proximal portions of the incision (made by the broader parts of the blade, for example through the sclera) has a larger cross section.

Generally, the cross-sectional size of the incision (at a given depth) is considered to be substantially the same as the cross-sectional size of the portion of the piercer that made the incision.

Generally, in such embodiments it is important that the cross sectional size of the distal tip of the injector be not less, and in some such embodiments greater than, the distal end of the incision. Consequently, during injection of the composition, there is little or no space between the scleral tissue and the distal tip of the injector. As a result, in some embodiments, the scleral tissue constitutes a seal (due to scleral tissue toughness and elasticity) around the distal tip of the injector.

Although not wishing to be held to any one theory, it is currently believed that when the dimensions of the distal tip of the injector are not less and even greater than that of the distal end of the incision, there is a tight fit of the sclera around the distal tip of the injector in the incision. When composition is injected, a hydraulic force develops in the subretinal area that leads to the observed substantially homogenous distribution of a composition in the subretinal space, in some embodiments including to the macula.

In some embodiments, a proximal end of the incision is larger than a distal end of the incision, and wherein during the inserting the injector, the distal tip of injector is advanced in the incision to no further than where the distal tip cross-sectional dimensions are greater than the incision, preferably within the sclera. For example, in the embodiments described above of a piercer comprising a blade having a pointed shape, the distal tip if the injector freely passes the proximal part of the incision (made by the broader parts of the blade) without substantial resistant until reaching a portion of the incision having a cross-section (made by a portion of the blade closer to the distal tip of the blade) that has the same or smaller cross section than the distal tip of the injector. In such a state, there is some resistance to further advancement of the injector and the walls of the incision provide a seal around the tip of the injector.

In some embodiments, the piercer is inserted into the eye at an acute angle relative to the outer surface of the eye. In some embodiments, the angle is not more than about 45°, not more than about 30° and even not more than about 20°. In some embodiments, the angle is not less than 1°, not less than about 2° and even not less than about 3° relative to the surface of the eye. In some embodiments, the angle is between about 45° and about 3°, between about 30° and about 10°, and even between about 25° and about 15° relative to the outer surface of the eye.

Although not wishing to be held to any one theory, it is currently believed that in such embodiments, the acute angle of the incision reduces the chance of passing through the subretinal space during the insertion of the piercer that would potentially damage the retina. Further, in some embodiments the acute angle helps ensure that the incision through the sclera is sufficiently long to allow the pierced sclera to seal around the portion of the injector in the incision in a way that leads to a distribution of pressure in the eye that leads to a homogenous distribution of a composition in the subretinal space. Additionally, in some embodiments, the longer incision produced by a piercer inserted into the eye at an acute angle heals more easily with less bleeding than a shorter incision.

In some embodiments, the method further comprises, during the inserting of the piercer and the inserting of the injector:

positioning a guide in a substantially fixed position relative to the eye;

inserting the piercer through the guide to assist in making the incision (e.g., with regards to the position of the incision and angle relative to the outer surface of the eye);

inserting the injector through the guide to assist in ensuring that the injector is inserted through (and preferably co-axially with) the incision.

In some embodiments, the method further comprises contacting an eye-contacting surface of the guide with a surface of the eye, in some embodiments thereby substantially fixing the relative position of the guide to the eye, analogously to the use of the Invitria® Intravitreal Injection Assistant designed by Dr. Arnaldo Gonçalves, M.D. of the Netherlands.

In some embodiments, contacting the eye-contacting surface of the guide with the surface of the eye, substantially immobilizes the eye, analogously to the use of the Invitria® Intravitreal Injection Assistant designed by Dr. Arnaldo Gonçalves, M.D. of the Netherlands.

In some embodiments, the guide is used to apply pressure to the eye through the eye-contacting surface that induces an anesthetic effect, analogously to the use of the Invitria® Intravitreal Injection Assistant designed by Dr. Arnaldo Gonçalves, M.D. of the Netherlands.

In some embodiments, the method further comprises, during the inserting of the piercer and the inserting of the injector, partially flattening the eye near the incision. In some embodiments, a guide (substantially as described above) is used to partially flatten the eye, for example, by applying pressure to surface of the eye through an eye-contacting surface. In some embodiments, such flattening makes it easier to make an incision of the desired depth. In some embodiments, after the flattened eye is allowed to revert to the usual curved shape, the incision is sealed better than otherwise due to the elasticity of the sclera, especially when the incision is a slit. As a result, in some embodiments, such flattening reduces the extent of bleeding and/or assists in post-operative healing.

Generally, when implementing the method and prior to making the incision with the piercer and, when relevant, prior to contacting a guide with the eye, the area of the eye is prepared for surgery in the appropriate way, for example with the use of antiseptics such as povidone-iodine.

In some embodiments local or general anesthesia is optionally administered. Local anesthetics may comprise an aminoamide (such as articaine, bupivacaine, dubicaine, etidocaine, levobupivacaine, lidocaine, mepivacaine, prilocaine, ropivacaine or trimecaine) or an amino ester (such as benzocaine, chloroprocaine, cocaine, cyclomethylcaine, dimethocaine, piperocaine, propoxycaine, novocaine, proparacaine, or teteracaine), or a combination local anesthetic such as lidocaine/prilocaine.

In some embodiments of the method, an eyelid speculum is used to retain the eyelid of the subject in an open position for at least some of the procedure.

Upon completion of the injection if composition, the injector is withdrawn from the incision and, if relevant, the guide removed from the eye.

The method for subretinal delivery described above may be implemented using any suitable device or collection of devices. That said, in some embodiments the method is preferably implemented using a device or a kit suitable for subretinal delivery of a composition as described herein.

According to an aspect of some embodiments of the invention there is provided a device suitable for subretinal delivery of a composition, comprising:

a guide configured to make contact with a surface of an eye of a subject (human or non-human mammal);

a piercer configured for making an incision through the sclera (and retinal pigment epithelium) to the subretinal space of the eye, when inserted through the guide; and an injector, for subretinal injection of a therapeutic composition when the injector is inserted through the guide into an incision made by the piercer.

According to an aspect of some embodiments of the invention there is also provided a kit suitable for subretinal delivery of a composition, comprising:

a guide configured to make contact with a surface of an eye of a subject (human or non-human mammal);

a piercer configured for making an incision through the sclera (and retinal pigment epithelium) to the subretinal space of the eye, when inserted through the guide; and an injector, for subretinal injection of a therapeutic composition when the injector is inserted through the guide into an incision made by the piercer.

According to an aspect of some embodiments of the invention there is provided a guide suitable for assisting in the subretinal delivery of a composition, the guide configured to guide a piercer to make an incision in the sclera of the desired dimensions and angle to the subretinal space of an eye, and the guide also configured to guide an injector into the incision (in some embodiments, substantially coaxially to the incision) in order to properly inject the composition into the subretinal space. In some embodiments, the guide is configured to be hand-held during use for subretinal delivery of a composition.

In some embodiments, the piercer and/or guide are configured to help substantially avoid making an incision that passes through the subretinal space to pierce the sensory retina.

A guide of a device or kit as described herein is configured to make contact with a surface of an eye of a subject during the use of the device or kit for subretinal delivery of a fluid composition. The guide is configured to guide the piercer so that the incision made in the sclera is of the desired dimensions and angle. The guide is also configured to guide the injector into the incision (in some embodiments, substantially coaxially to the incision) in order to properly inject the composition into the subretinal space. In some embodiments, the guide is configured to be hand-held during use for subretinal delivery of a composition.

In some embodiments, the guide comprises an open-ended guide channel for accepting the piercer and thereby guiding the insertion of the piercer to make the incision, and for accepting the injector and thereby guiding the insertion of the injector into the incision made by the piercer. In some embodiments, the guide comprises an open-ended channel having a proximal end (opening) and a distal end (opening), the guide channel configured for accepting the piercer and the injector, allowing insertion of the piercer and the injector therethrough. Specifically, in some embodiments, a piercer inserted through the guide channel from the proximal end emerges from the distal end and is thereby guided to make a desired (e.g., in terms of location and angle) incision in the sclera of an eye. Specifically, in some embodiments, an injector inserted through the guide channel from the proximal end emerges from the distal end and is thereby accurately guided (in some embodiments, coaxially) into an incision made by the piercer.

In some embodiments, the guide further comprises a movable retainer for retaining the piercer when making an incision and for retaining the injector when injecting a therapeutic composition. In some embodiments, the movable retainer is configured to slide inside the guide channel while retaining the piercer or the injector. In some embodiments, a retainer comprises a spring-loaded piston.

In some embodiments, the guide channel is configured so that when the guide contacts (properly for the intended use) an eye of a subject, the guide channel is at an acute angle relative to a surface of the eye near a distal end of the guide channel. In some embodiments, the angle is not more than about 45°, not more than about 30° and even not more than about 20°. In some embodiments, the angle is not less than 1°, not less than about 2° and even not less than about 3° relative to the surface of the eye. In some embodiments, the angle is between about 45° and about 3°, between about 30° and about 10°, and even between about 25° and about 15° relative to the outer surface of the eye.

In some embodiments, the guide comprises an eye-contacting surface configured to make contact with a surface of an eye during use of the device. In some embodiments, when the eye-contacting surface contacts an eye, the position of the guide is substantially fixed in relation to the eye.

In some embodiments, the eye-contacting surface of the guide is configured for contacting at least a portion of the front outer surface of an eye of a specific species of subject. The eye-contacting surface is preferably suitably configured for contacting the eye of a mammalian eye, including a human eye, for example, analogously to the eye-contacting surface of the Invitria® Intravitreal Injection Assistant designed by Dr. Arnaldo Gonçalves, M.D. of the Netherlands.

In some embodiments, the eye-contacting surface is configured to surround but avoid substantial contact with the cornea of the eye of a subject during use. In some such embodiments, the eye-contacting surface has a shape that is substantially a complete or partial ring.

In some embodiments, the eye-contacting surface is curved to substantially follow the curvature of a contacted surface of an eye.

In some embodiments, the eye-contacting surface is configured to at least partially flatten the curvature of a contacted surface of an eye. In some such embodiments, the flattening allows greater control of the depth of the incision in the sclera made by the piercer. In some such embodiments, the eye-contacting surface is substantially flat.

In some embodiments, the guide comprises a guide body extending from the eye-contacting surface. In some embodiments, the guide body is configured, e.g., in terms of size and shape, to be grasped with a human hand allowing a user to manually hold the device during use, especially to make and maintain contact with a surface of an eye.

In some embodiments, the guide body defines a hollow configured to maintain a fluid (for example, ultrasonic gel) in contact with a surface of a contacted eye. In some embodiments, the hollow is configured, e.g., in terms of size and shape, to accept a component of an imaging modality when the guide is in contact with a surface of an eye, allowing the imaging modality to be used for imaging at least a portion of the contacted eye. For example, in some embodiments, the hollow is configured to accept an ultrasonic probe such as a UBM (ultrasonic biomicroscopy) probe, allowing observation of the progress (especially depth) of the piercer making an incision in the sclera of the eye.

A guide may be fashioned from any suitable material. Generally, a suitable material is rigid, hypoallergenic and suitable for contacting an outer surface of an eye, such as, for example, polycarbonate, cellulose propionate, acetate propionate, polyamides, metals (including titanium, beryllium, stainless steel, aluminum) and the like. In some embodiments, the guide is disposable, and intended for single use, provided within a sealed, sterile, package. In some embodiments, the guide is fashioned from a material which is able to withstand sterilization for repeated use.

A piercer of a device or kit as described herein is configured for making an incision in the sclera of the eye when inserted through the guide, to the subretinal space. In some embodiments, the piercer is configured to be hand-held for use. For example, in some embodiments for use a user holds the guide with one hand and the piercer with the other hand.

Generally, the piercer is an elongated piercer comprising a distal end with a distal piercing tip, the piercing tip of sufficient sharpness to pierce the sclera, choroid and retinal pigment epithelium of an eye to make an incision. Generally, the distal end of the piercer is configured to be inserted through the guide while the guide makes contact with an eye. In such a way, the guide assists (e.g., in terms of angle and position) in making the required incision in the sclera of the eye. In some embodiments, the distal end of the piercer is configured to be inserted through a guide channel in the guide. In some such embodiments, the distal end of the piercer is longer than the channel.

In some embodiments, a part of the piercer (e.g., the distal end or a part near the distal end) is configured to intimately contact at least a portion of a guide channel of a guide such that the piercing tip can be moved axially to pierce an eye but lateral movement of the piercer is substantially limited.

The distal end of the piercer may be of any suitable shape. In some embodiments, the distal end of the piercer is flat so that an incision made by the piercer in a sclera is a slit. Thus, in some embodiments, the piercer is configured to make an incision that is a slit. In some such embodiments, the distal end of the piercer has a thickness (height) and a width, the width being not less than 150% and even not less than 200% of the thickness.

As discussed herein, in some embodiments the injector is an elongated injector having a distal end and distal tip, the distal tip of the injector having cross-sectional dimensions not smaller, and in some embodiments greater, than a distal end of an incision made by the piercer. In such embodiments, when the injector is inserted through the guide to enter the incision made by the piercer, the injector easily slides through the incision with little resistance until the distal tip of the injector reaches a portion of the incision that has a cross-sectional dimension the same or less than of the distal tip of the injector. In some embodiments, the piercer is configured to make an incision having a proximal end (near the entry point) larger than a distal end (near the subretinal space), for example, in some such embodiments, the distal piercing tip is tapered, e.g., pointed.

In some embodiments, the distal end of the piercer comprises a blade, in some embodiments having a pointed shape (e.g, triangular, leaf-shaped) from the distal tip of the blade. In some embodiments, the blade is a flat triangular blade, e.g., concave triangle, straight-edged or convex triangle or a flat leaf-shaped blade.

The cross-sectional dimensions of the distal end of the piercer, that ultimately define the size of an incision made in a sclera, are any suitable dimensions. In some embodiments, the width of the distal end of a piercer are in the range of between about 0.5 mm and about 2 mm.

As discussed above, the piercer is used to make an incision from an outer surface of the eye through the sclera to the subretinal space, preferably without piercing the sensory retina. In some embodiments, a user sees that the incision is of the proper depth by the appearance of blood that was transported from the subretinal space, in a proximal direction through the incision along the piercer to be apparent at the entrance point of the piercer into the sclera. In some embodiments, the piercer comprises a groove passing from at or near the distal tip of the piercer in a generally proximal direction. Such a groove helps transport blood from the subretinal space in a proximal direction to be apparent at the entrance point of the piercer into the sclera.

Generally, a piercer comprises, in addition to a distal end with a distal piercing tip, a handle to facilitate gripping of the piercer prior to and during use thereof.

The total length of the piercer may be any suitable length for ease and convenience of use. For example, in some embodiments the length of the piercer is in the range of from about 10 cm to about 25 cm.

The piercer may be made of any suitable material, including, but not limited to, polymers, metals and composites. In some embodiments, a piercer is made of a stainless steel.

An injector of a device or kit as described herein is configured for subretinal injection of a therapeutic composition when the injector is inserted through the guide into the incision made by the piercer. In some embodiments, the injector is configured to be hand-held for use. For example, in some embodiments a user holds the guide with one hand and the injector with the other hand.

In some embodiments, the injector is an elongated injector having a distal end and distal tip, the distal tip having cross-sectional dimensions not smaller than a distal end of an incision made by the piercer in a sclera. In some embodiments, the distal tip of the injector having cross-sectional dimensions greater than of a distal end of an incision made by the piercer in a sclera. In some such embodiments, the distal tip of the injector has a cross-sectional dimension smaller than the proximal end of the incision at the entry point into the sclera so that the distal tip of the injector easily fits, with no substantial resistance, into the incision. The distal tip of the injector can be advanced deeper in the incision until a portion of the incision is reached that is the same or smaller in cross sectional dimension than the distal tip of the injector, increasing resistance to further insertion of the injector. In such a way, a user is able to advance the injector to a desired depth without excessive penetration.

In some embodiments, the distal tip if the injector is blunt, e.g., comprises a blunt hollow delivery needle. As during use of the device an incision is made in the sclera with a separate piercer and the injector is passed through the incision, the use of a blunt injector reduces the chance of undesired damage to the eye. In some embodiments, a blunt tip prevents excessive penetration in the incision. In some embodiments, a blunt tip contacts the surrounding walls of a distal part of an incision, making an effective seal.

In some embodiments, the injector comprises a delivery needle having an outer diameter of not more than about 2 mm, not more than about 1 mm and even not more than about 0.5 mm.

As noted above, the injector is inserted through the guide to enter the incision made by the piercer. To assist in ensuring that the injector enters into the incision, in some embodiments, a part of the injector (e.g., the distal end or a part near the distal end) is configured to intimately contact at least a portion of a guide channel of a guide such that the distal tip of the piercer can be moved coaxially to the incision, but lateral movement of the injector is substantially limited.

In some embodiments, the injector further comprising a reservoir for containing a composition.

In some embodiments, the reservoir is filled just prior to use, for example by medical personnel participating in a treatment that makes use of the device.

In some embodiments, the device or the kit further comprise a therapeutic composition contained in the reservoir (e.g., are provided pre-charged), especially a therapeutic composition for the treatment of an eye disorder. In some such embodiments, the reservoir is filled with a required dose of a therapeutic composition.

In some embodiments, the reservoir is sized to contain a desired amount of the therapeutic composition to be dispensed., for example, in some embodiments between about 10 and about 100 microliters, in some embodiments between about 15 and about 75 microliters, and in some embodiments between about 25 and about 50 microliters.

During use, once the injector is properly positioned in the incision made by the piercer, the composition is transported from the reservoir through the injector into the subretinal space, thereby administering the composition.

The injector is fashioned of any suitable material, including, but not limited to, polymers, metals and composites. In some embodiments, the injector is made of a stainless steel.

In some embodiments, the injector together with the reservoir comprising a syringe. In some embodiments, the injector together with the reservoir comprises a standard glass or plastic medical syringe.

In some embodiments, the injector comprises an infusion pump, that is to say a pump configured to automatically deliver a specified amount of composition in a specific period of time, allowing a more accurate control of pressure and rate of injection of a composition.

The devices, methods and kits of described herein may be used to deliver a therapeutic composition (especially a liquid therapeutic composition) to the subretinal space of a mammalian eye, such as a composition including a pharmaceutically effective amount of an active ingredient (e.g., an active pharmaceutical ingredient and/or a cell and/or a gene) in a suitable carrier.

The amount of therapeutic composition administered is any suitable amount and depends on factors such as the nature of the active ingredient, the concentration of the active ingredient, the treatment circumstances and the professional judgment of a treating physician and is readily calculable by one of ordinary skill in the art without undue experimentation. That said, typically the amount of composition administered to a human eye is up to about 100 microliters, up to about 75 microliters, more typically up to about 50 microliters. Typically, an amount of composition administered is between about 10 microliters and about 50 microliters.

As used herein a "therapeutic composition" refers to a preparation of one or more of the active ingredients with other components such as pharmaceutically-acceptable carriers and excipients. The purpose of a therapeutic composition is to facilitate administration of an active ingredient to a subject.

The term "pharmaceutically acceptable carrier" refers to a carrier or a diluent that does not cause significant irritation to a subject and does not substantially abrogate the activity and properties of the administered active ingredients. An adjuvant is included under these phrases. The term "excipient" refers to an inert substance added to a therapeutic composition to further facilitate administration of an active ingredient.

Therapeutic compositions used in implementing the teachings herein may be formulated using techniques with which one of average skill in the art is familiar in a conventional manner using one or more pharmaceutically-acceptable carriers comprising excipients and adjuvants, which facilitate processing of the active ingredients into a pharmaceutical composition and generally includes mixing an amount of the active ingredients with the other components. Suitable techniques are described in "Remington's Pharmaceutical Sciences," Mack Publishing Co., Easton, Pa., latest edition, which is incorporated herein by reference. For example, pharmaceutical compositions useful in implementing the teachings herein may be manufactured by one or more processes that are well known in the art, e.g., mixing, blending, homogenizing, dissolving, granulating, emulsifying, encapsulating, entrapping and lyophilizing processes.

Pharmaceutical compositions suitable for implementing the teachings herein include compositions comprising active ingredients in an amount effective to achieve the intended purpose (a therapeutically effective amount). Determination of a therapeutically effective amount is well within the capability of those skilled in the art, for example, is initially estimated from animal models such as monkey or pigs.

In accordance with the above, a therapeutic composition used for implementing the teachings herein includes any suitable carrier. In some embodiments, a suitable carrier is PBS (phosphate buffered saline, e.g., 140 mM NaCl, 2.8 mM KCl, 10 mM sodium phosphate dibasic, 2 mM potassium phosphate monobasic with a pH of 7.4).

A therapeutic composition used for implementing the teachings herein includes any suitable active ingredient. In some embodiments, a therapeutic composition comprises at least one active ingredient selected from the group consisting of at least one of an active pharmaceutical ingredient, a cell and a gene.

Suitable active ingredients include, but are not limited to, active pharmaceutical ingredients such as thrombin inhibitors; antithrombogenic agents; thrombolytic agents; fibrinolytic agents; vasospasm inhibitors; calcium channel blockers; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometholone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1,3-cis retinoic acid); decongestants (such as phenylephrine, naphazoline, tetrahydrazoline); miotics and anti-cholinesterase (such as pilocarpine, salicylate, carbachol9 acetylcholine chloride, physostigmine, serine, diisopropyl fluorophosphate, pholine iodine, demecarium bromide); antineoplastics (such as carmustine, cisplatin, fluorouracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotropin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, proteins, peptids and the like.

In some embodiments, a therapeutic composition comprises an anti-angiogenic agent such as ranibizumab, bevacizumab, or pegaptanib, or combinations thereof.

In some embodiments, a therapeutic composition comprises an anti-vascular endothelial growth factor (anti-VEGF) agent such as macugen, lucentis, avastin, or combinations thereof.

In some embodiments, a therapeutic composition comprises a cell is selected from the group consisting of a stem cell, a forebrain-derived human cortical neural progenitor cell, a retinal progenitor cell, a mature photoreceptor cell, and an RPE cell. In some embodiments, the stem cell is selected form the group consisting of hippocampal stem cells, embryonic stem cells, bone marrow stem cells and retinal stem cells.

In some embodiments, the teachings herein are used and/or implemented for the treatment of disorders of the eye such as retinitis pigmentosa, macular degeneration (including atrophic macular degeneration), Best's disease, Stargardt's disease, Sorsby's disease, juvenile macular degeneration, central areolar choroidal dystrophy, central serous chorioretinopathy, choroidermia, choroidal melanoma, Coat's disease, cone-rod dystrophy, corneal dystrophy, Fuch's dystrophy, cystoids macular edema, diabetic retinopathy, Doyne honeycomb retinal dystrophy, hypertensive retinopathy, juvenile retinoschisis, lattice degeneration, Leber's miliarly aneurism, ocular histoplasmosis, ocular ischemic syndrome, papillophlebitis, polypoidal choroidal vasculopathy, toxoplasmosis, and Usher syndrome, vascular occlusions, inflammations such as uveitis, choroiditis and retinistis, and various tumors including neoplasms.

In a preferred embodiment, the disease of the eye treated in accordance with the teachings herein is atrophic macular degeneration, and the therapeutic composition comprises stem cells as an active ingredient in a carrier such as PBS.

In some such embodiments, a concentration of between about 10,000 and about 60,000 cells/µl, in some embodiments between about 20,000 and about 40,000 cells/µl and in some embodiments between about 25,000 and about 35,000 cells/µl.

In some such embodiments, when the subject is human, between about 1 µl and about 50 µl, and in some embodiments between about 20 µl and about 40 µl, of therapeutic composition is administered.

An embodiment of a device suitable for subretinal injection of a composition in accordance with the teachings herein, device 10, is schematically depicted in FIGS. 1A-1F. Device 10, see FIG. 1A, is provided as a kit comprising three physically separate components, a guide 12, a piercer 14 and an injector 16 each provided sterilized in a separate sterility-maintaining package (not-depicted) e.g., manufactured by Westfield Medical Ltd., Somerset, United Kingdom.

Figure 1B:
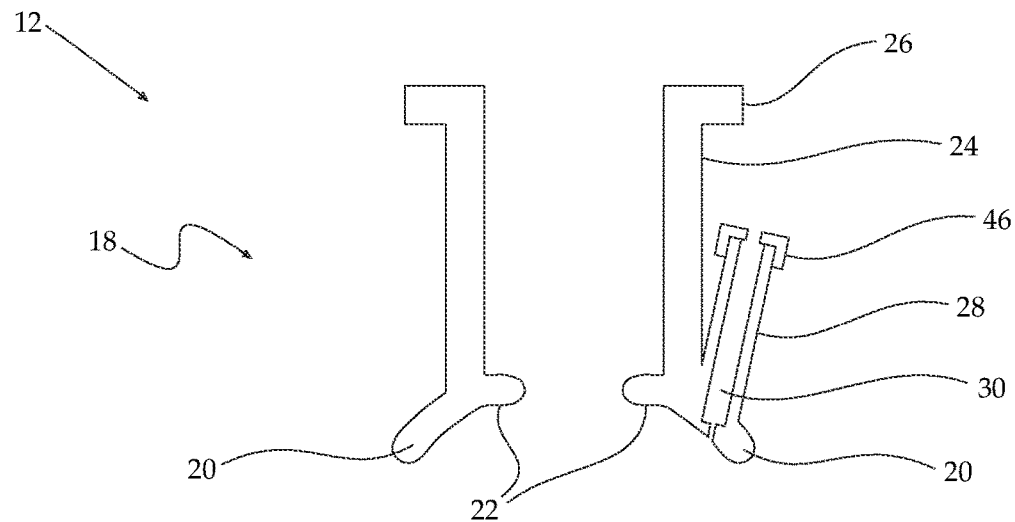
FIGS. 1B to 1D are schematic depictions of the guide of the device of FIG. 1A, in cross-section.

Guide 12 is schematically depicted in perspective in FIG. 1A and in side cross section in FIG. 1B. Guide 12, configured to be hand-held, comprises a single-piece injection-molded polycarbonate transparent guide body 18 that resembles the Invitria® Intravitreal Injection Assistant designed by Dr. Arnaldo Gonçalves, M.D. of the Netherlands and includes a ring-shaped base 20 with an eye-contacting surface 22, a substantially tubular guide body 24 extending substantially perpendicularly from base 20 ending with a flaring handle 26 configured for easy grasping by a human hand. A guide tube 28 extends from base 20 at an angle relative to guide body 24. Guide 12 is configured so that when guide 12 is in use in accordance with the teachings herein, eye-contacting surface 22 contacts a sclera and substantially follows the curvature of the surface of the eye while the "hole" in base 20 encircles the cornea without substantial contact.

Figure 1C:
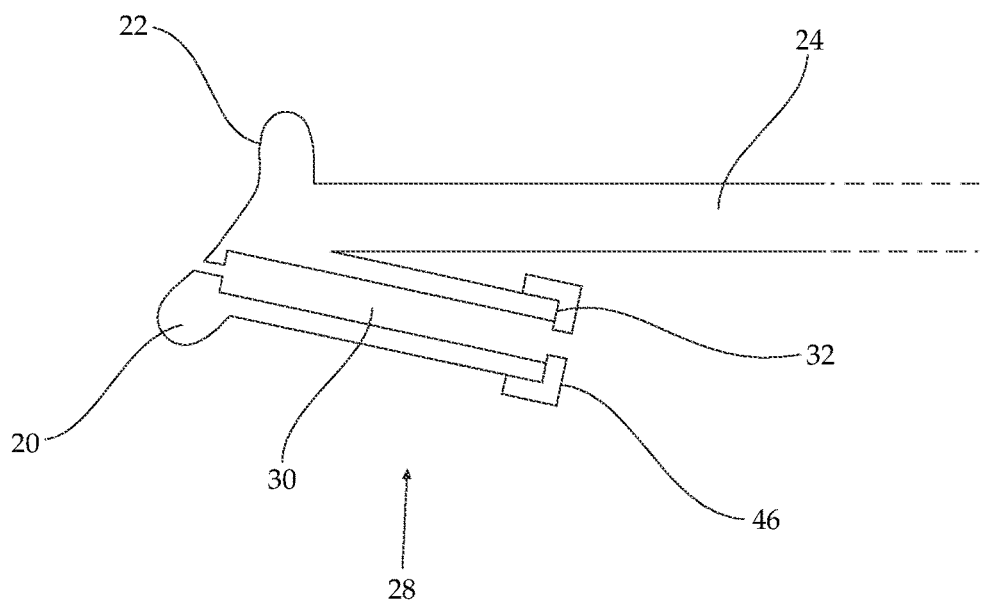
Figure 1D:
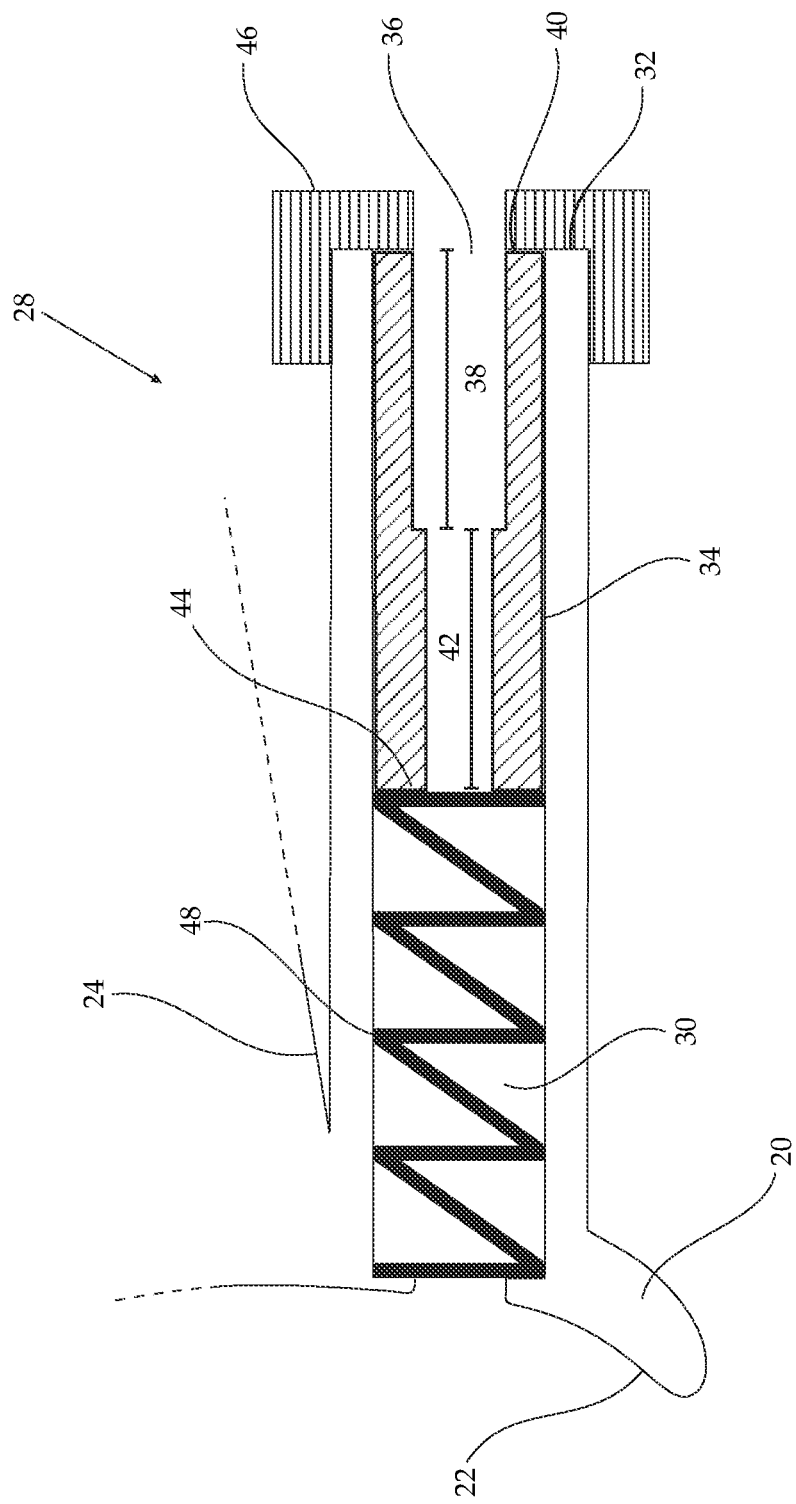

In FIGS. 1C and 1D, guide tube 28 is schematically depicted in side cross-section in greater detail. Passing through guide tube 28 and base 20 is a 4 cm long guide channel 30 angled 10° from parallel to tubular guide body 24.

From a proximal end 32 and through guide tube 28, guide channel 30 is a parallel-walled cylindrical channel with a 8 mm diameter that narrows to 5 mm at eye-contacting surface 22.

Slidingly-contained inside guide channel 30 is a 2 cm long 8 mm diameter polycarbonate tubular piston 34 defining an axial parallel-walled cylindrical piston-channel 36. A first half 38 of piston channel 36 from a proximal end 40 of piston 34 has a 4-mm diameter. A second half 42 of piston channel 36 from a distal end 44 of piston 34 has a 3-mm diameter. Piston 34 is configured to function as a movable retainer for retaining piercer 14 when making an incision in an eye and for retaining injector 16 when injecting a therapeutic composition.

Capping proximal end 32 of guide tube 28 and preventing piston 34 from exiting the confines of guide channel 30 is polycarbonate cap 46 having a 4-mm hole therethrough.

8 mm-outer diameter coil spring 48 of surgical stainless steel is contained inside guide channel 30 between eye-contacting surface 22 and distal end 44 of piston 34, biased to apply a force pushing piston 34 towards cap 46.

Figure 1E:
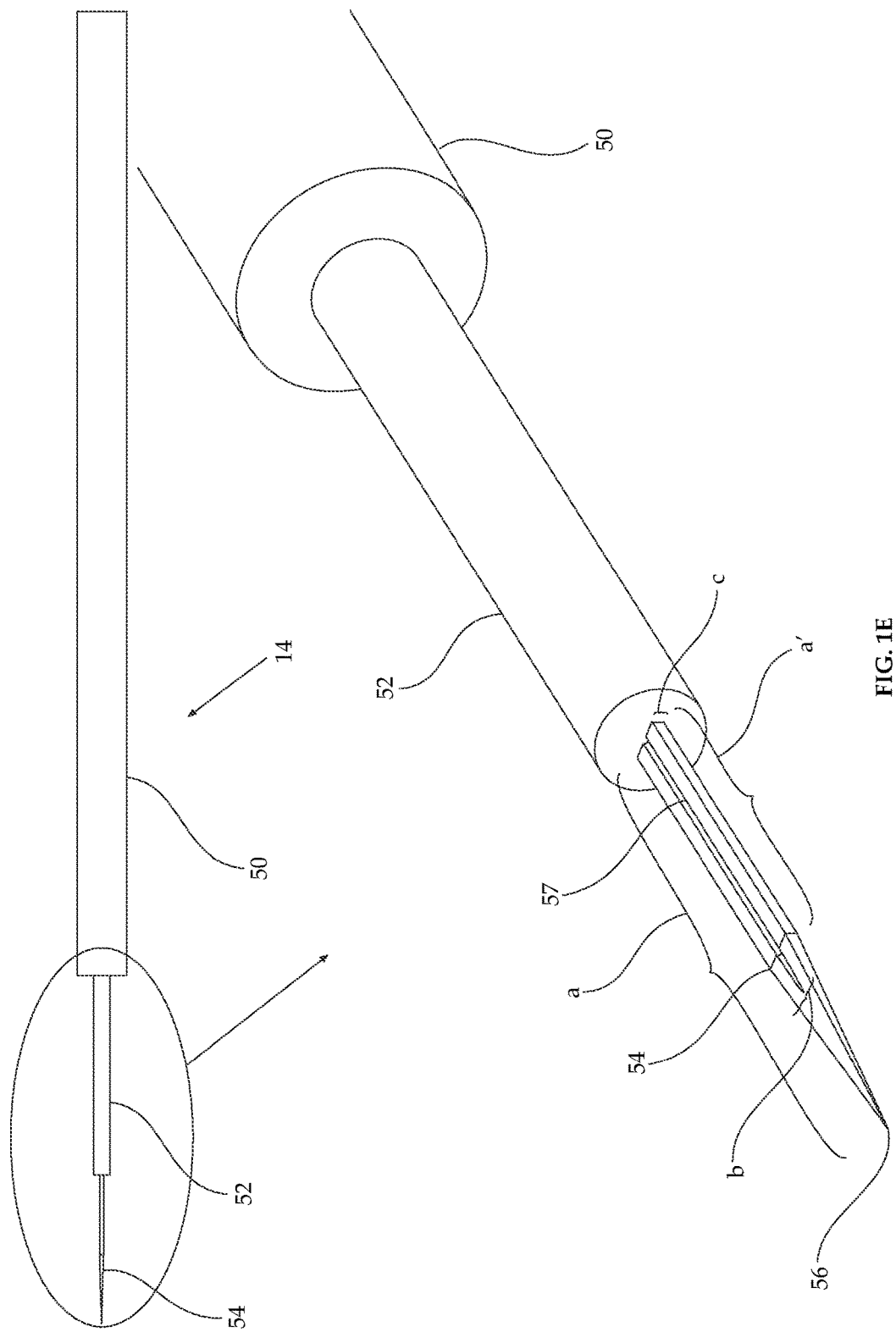
FIG. 1E is a schematic depiction of the piercer of the device of FIG. 1A.

Piercer 14, schematically depicted in detail in FIG. 1E, is a single-piece component of surgical stainless steel having three distinct sections: a 12-cm long 10-mm diameter round handle section 50 having a texture to be conveniently held by a human, a 3-cm long 4-mm outer diameter cylindrical stem section 52; and a flat distal piercing section 54 18 mm long (dimension a) configured to make a slit incision. The 12 mm long proximal part (dimension a') of piercing section 54 has a rectangular cross section that is 1 mm wide (dimension b) and 0.3 mm thick (dimension c). The 8 mm long distal part of piercing section 54 is a straight edged triangular pointed blade tapering both in the height dimension and width dimension to distal piercing tip 56. Distal piercing section 54 also comprises a 0.5 mm deep groove 57 for assisting in transporting blood in a proximal direction from piercing tip 56.

Piercer 14, together with spring 48 and piston 34 are configured to help make the incision to the subretinal space of an eye and also to substantially avoid making an incision that passes through the subretinal space to pierce the sensory retina, and if the sensory retina is pierced, to substantially limit the extent of damage caused to the eye.

Figure 1F:
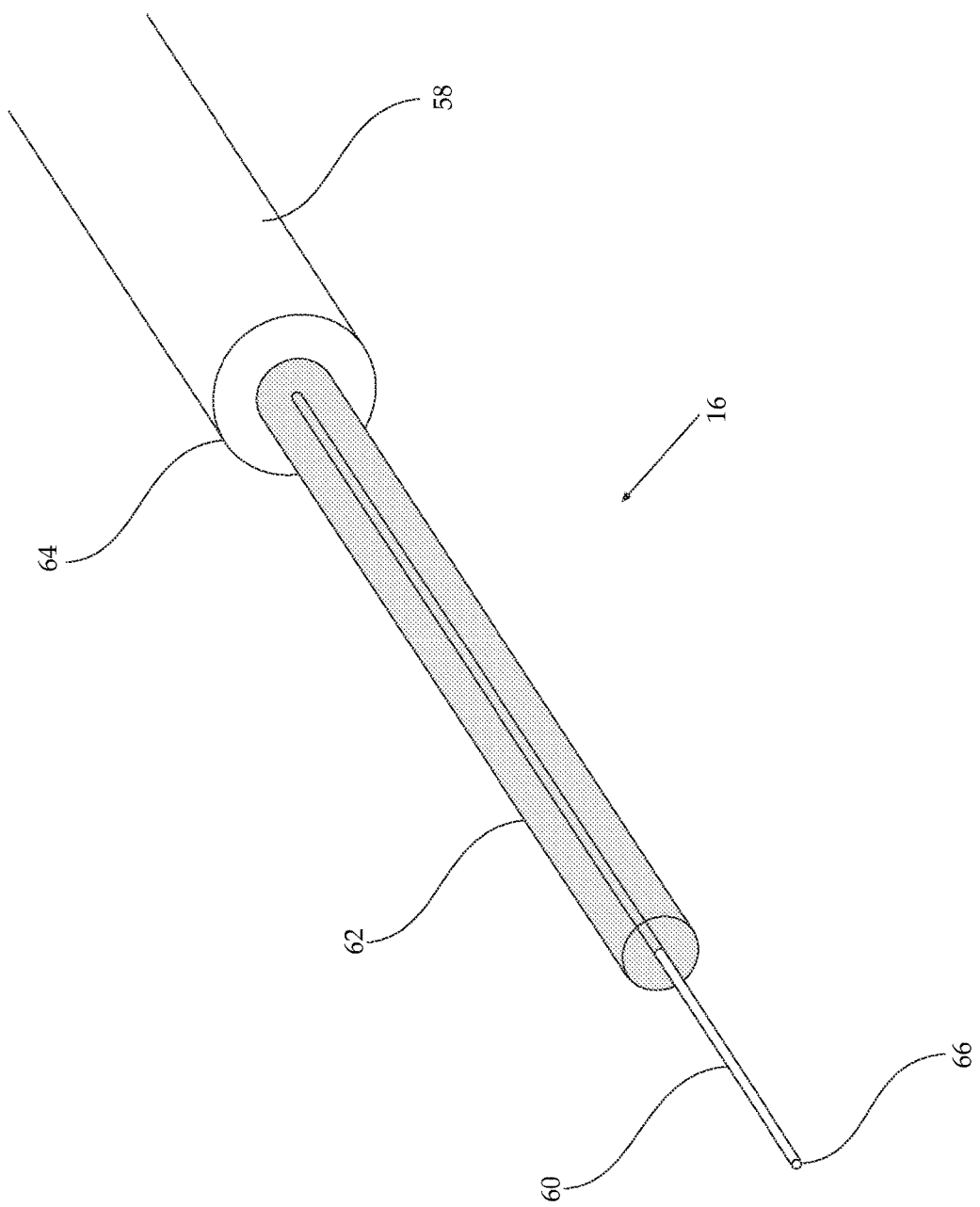
FIG. 1F is a schematic depiction of the distal end of the injector of the device of FIG. 1A.

Injector 16, which distal end depicted in detail in FIG. 1F, is a standard glass 50-microliter syringe 58 (e.g., available from Hamilton Bonaduz AG, Bonaduz, GR, Switzerland) with a (30 gauge) 0.31 mm outer diameter injection needle 60 encircled by a 4-mm outer diameter high-density polyethylene sheath 62 from a syringe barrel 64 to 20 mm from a blunt needle tip 66.

For use, guide 12 is removed from a respective sterility-preserving package and placed against the eye of a subject in a manner analogous to the use of the Invitria® Intravitreal Injection Assistant designed by Dr. Arnaldo-Gonçalves, M.D. of the Netherlands. Specifically, the eyelids of a subject are moved apart to expose the eye and eye-contacting surface 22 is pushed against the anterior portion of the eye so that eye-contacting surface 22 contacts the sclera and substantially follows the curvature of the surface of the eye while the "hole" in base 20 encircles the cornea without substantial contact therewith. Guide 12 is gently rotated using handle 26. In such a way, guide 12 is in a substantially fixed position relative to the eye, the eye becomes fixated and the subject feels an anesthetic effect due to the pressure. The eye of the subject is unable to move or see the rest of the procedure. Guide tube 28 and guide channel 30 are directed at an acute angle relative to the surface of the eye.

Piercer 14 is removed from a respective sterility-preserving package and held by an operator (e.g., an eye surgeon) by handle section 50. Piercing tip 56 is threaded into the hole in cap 46 and advanced forward inside piston channel 36 until 1 cm of the distal end of stem section 52 is contacts the distal end of first half 38 of piston channel 36.

In such a position, 1 cm of the 3 cm of stem section 52 of piercer 14 is in intimate contact with first half 38 of piston channel 36, the 12 mm proximal part of piercing section 54 is substantially entirely inside second half 42 of piston channel 36 except for 2 mm that protrude distally therefrom, and the 8 mm distal part of piercing section 54 are inside the bore of spring 48 in guide channel 30. Piercer 14, and particularly piercing section 54, are prevented from moving laterally relative to the axis of guide channel 30 due to the intimate contact of piston 34 with guide channel 30 and of stem section 52 with proximal end 40 of piston channel 36.

The operator carefully pushes piercer 14 distally through guide 12, so that the distal end of stem section 52 pushes piston 34 to slide distally inside guide channel 30 against the return force applied by spring 48. After about 12 mm, piercing tip 56 pierces and penetrates into the surface of the eye. Piercer 14 thus makes an incision in the sclera of the eye at 10° relative to the axis of guide body 18 at an acute angle to the surface of the eye. The distal end of the incision is narrower than the proximal end of the incision.

Due to the approximately 18 mm stroke of piston 34 inside guide channel 30, piercing tip 56 is prevented from extending more than about 6 mm from contact surface 22 into the eye. For an added level of safety, when piercer is pushed 1.8 cm through guide tube, the distal end of handle section 50 of piercer 14 contacts cap 46, preventing any further advancement of piercing tip 56. The limit to the depth to which piercing tip 56 can penetrate into the eye prevents catastrophic damage to the eye in case of accident.

When piercer 14 advances, piercing tip 56 passes the sclera and the retinal pigment epithelium to the subretinal space. When piercing tip 56 enters the subretinal space, blood passes in a proximal detection along the piercing section of piercer 14, also through groove 57.

At the first appearance of blood, indicative that piercing tip 56 has reached the subretinal space of the eye, the operator pulls back and withdraws piercer 14 from guide 12.

Injector 16 is removed from a respective sterility-preserving package and charged in the usual way with 50 microliters of fluid therapeutic composition, e.g., 30,000 stem cells/microliter in PBS composition. Blunt needle tip 66 of injector 16 is guided through the hole in cap 46 into piston channel 36 until the distal end of sheath 62 contacts the end of first half 38 of piston channel 36, and needle tip 66 passes through second half 42 of piston channel 36 to protrude 12 mm from distal end 44 of piston 34.

The operator carefully pushes injector 16 distally, so that the distal end of sheath 62 pushes piston 34 to slide distally inside guide channel 30 against the return force applied by spring 48. Blunt needle tip 66 enters the incision in the sclera made by piercer 14 and advances coaxially with no substantial resistance except of spring 48 in the incision. A sudden increase of resistance to further advancement indicates that needle tip 66 is in contact with a portion of the incision that has substantially the same or a narrower cross sectional size than of needle tip 66. The operator uses injector 16 in the usual way to inject the therapeutic composition. The composition passes through needle tip 16 and into the distal end of the incision into the sub retinal space.

In accordance with the teachings herein, the injection of the composition leads to a relatively homogenous distribution of the composition in a large portion of the subretinal space of the eye, including to the macula.

Figure 2A:
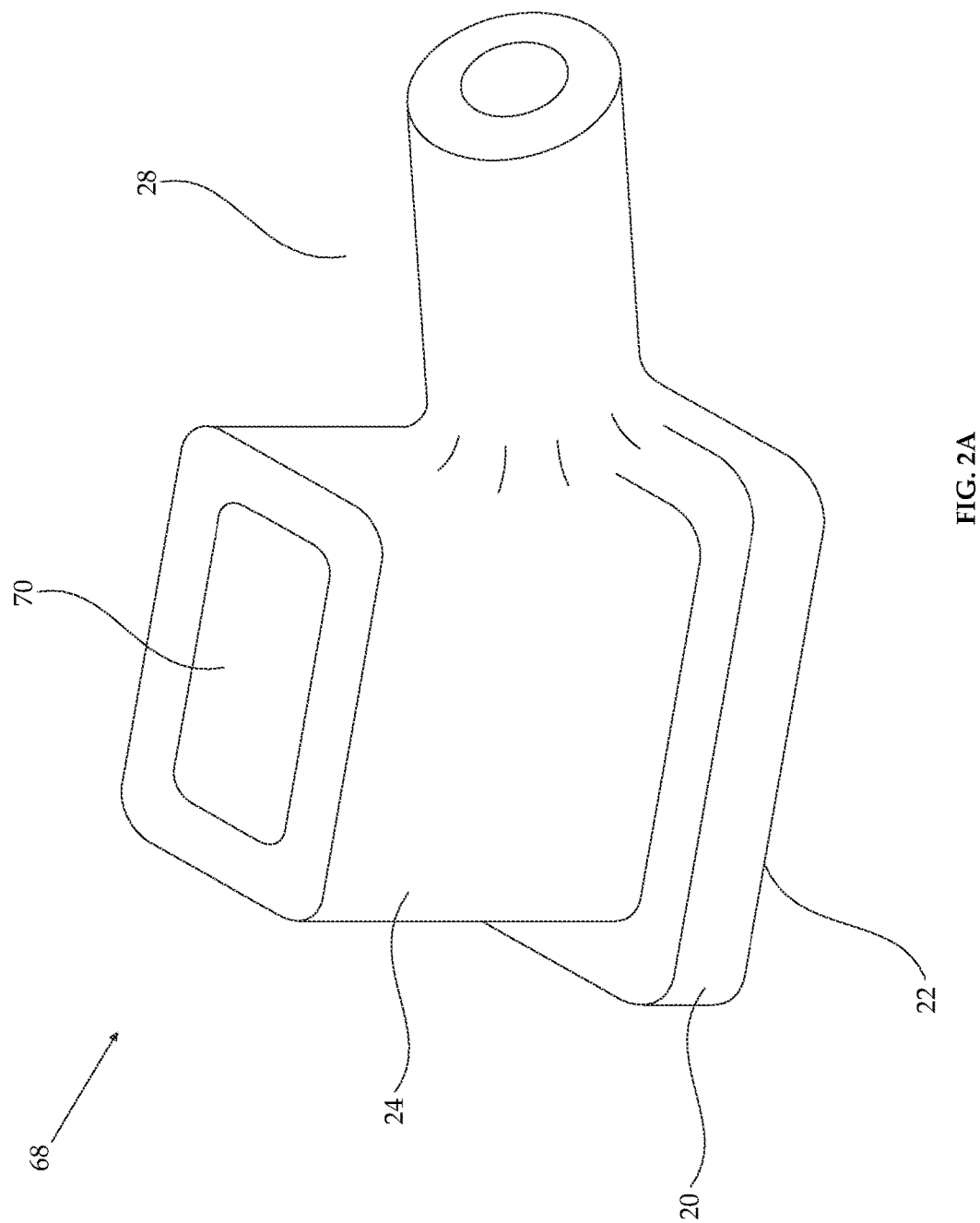

A guide 68 of an additional embodiment of a device suitable for subretinal injection of a composition in accordance with the teachings herein, device, is schematically depicted in FIG. 2A (perspective view), 2B (bottom view) and 2C (side cross section).

Guide 68 comprises a single-piece injection-molded polycarbonate transparent guide body 18 and includes a 3-mm high, 20-mm long, 12-mm wide rounded-corner rectangular base 20 with a flat eye-contacting surface 22. Guide 58 is configured so that when guide 58 is in use in accordance with the teachings herein, eye-contacting surface 22 contacts a sclera at an outer side of the eye and partially flattens a contacted surface of the eye.

Extending substantially perpendicularly from base 20 is a 15-mm high, 15-mm long, 8 mm wide guide body 24. The walls of guide body 24 are 2 mm thick so that guide body 24 defines an 11-mm long, 4-mm wide, 18-mm deep open-ended hollow 70 that passes from the top of guide 68 through eye-contacting surface 22. Guide 68 is configured to be hand-held by grasping of guide body 24, although use with a fixed support is also possible.

A 5-mm outer diameter 12.5-mm long guide tube 28 extends from base 20 at a 15° angle from eye-contacting surface 22. Passing through guide tube 28 and base 20 to emerge into hollow 70 at eye-contacting surface 22 is a 15-mm long circular guide channel 30 with a 10-mm long 2-mm wide proximal section 72 and a 5-mm long 0.9-mm wide distal section 74.

Figure 2B:
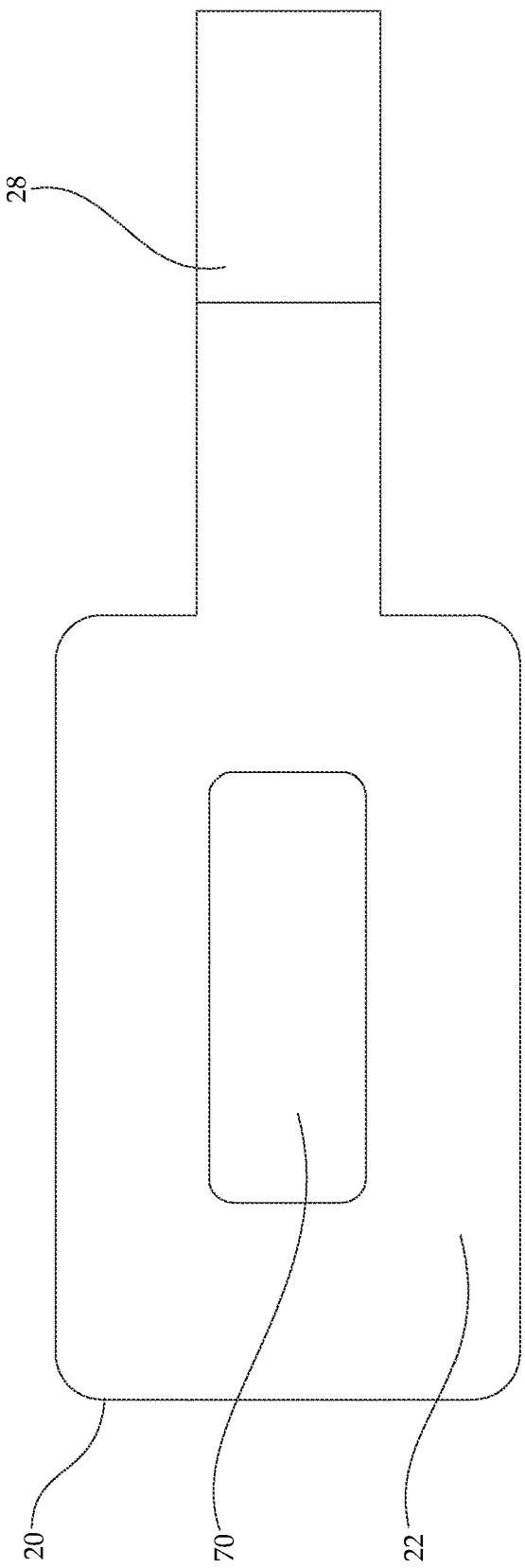
Figure 2D:
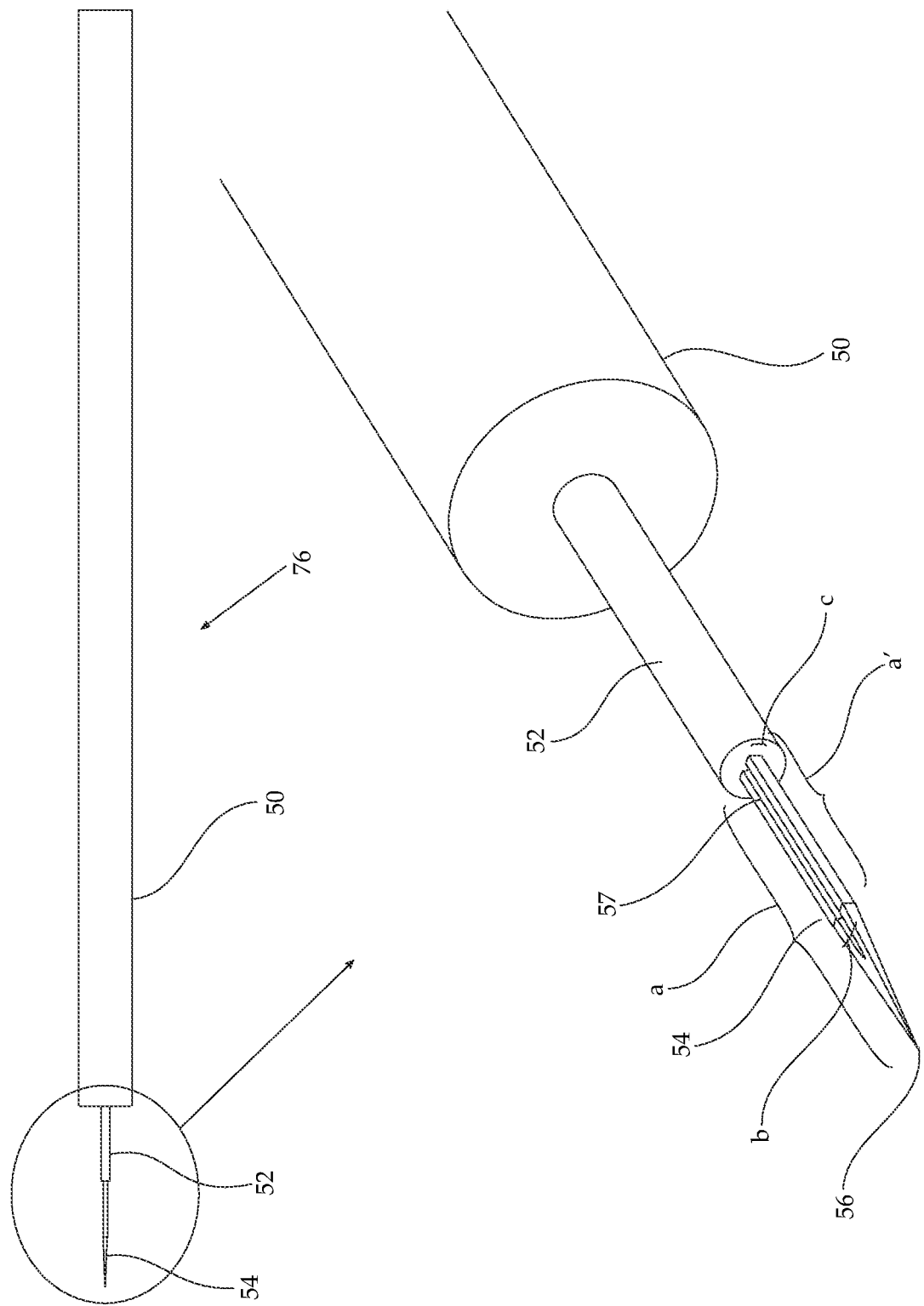
FIG. 2D is a schematic depiction of the piercer of the device of FIG. 2A.

In FIG. 2D, a piercer 76 for use with guide 68 is schematically depicted. Piercer 76 is substantially similar to piercer 14 of device 10 includes a 12-cm long 10-mm outer diameter handle section 50, a 10-mm long 2-mm diameter stem section 52, and a 13-mm long 0.9-mm wide 0.3-mm thick piercing section 54, substantially a flat triangular blade tapering to a piercing tip 56.

As discussed in detail below, guide channel 30 and piercer 76 are together configured to help make the incision to the subretinal space and to substantially avoid making an incision that passes through the subretinal space to pierce the sensory retina, and if the sensory retina is pierced, to substantially limit the extent of damage caused to the eye.

For use, guide 68 is removed from a respective sterility-preserving package and positioned against a side of the eye of a subject, as far away from the retina as possible, with the proximal end of guide tube 28 extending forward so that distal end of guide channel 30 is directed towards the back of the eye. Guide 68 is pressed downwards so that the position of guide 68 is substantially fixed relative to the eye and so that the surface of the eye in contact with eye-contacting surface 22 is at least partially flattened.

A suitable ultrasonic gel is placed inside hollow 70 to make contact with the surface of the eye. The distal tip of a UBM probe functionally associated with a UBM imaging modality (ultrasound biomicroscopy such as Vevo 660, VisualSonics, Inc., Toronto, Canada) is immersed in the gel. The UBM imaging modality is activated to continuously acquire images of the subretinal space of the eye below hollow 70.

Piercer 76 is removed from a respective sterility-preserving package and held by an operator by handle section 50. The operator inserts piercing tip 56 of piercer 76 into the proximal end of guide channel 30.

When piercing tip 56 of piercer 76 is inserted into and through guide channel 30 and stem section 52 is 3 mm inside proximal section 72 of guide channel 30, piercing tip 56 of piercer 76 slightly protrudes from the distal end of guide channel 30 but is about 0.8 mm from the surface of the eye. In such a position, stem section 52 is in intimate contact with proximal section 72 of guide channel 30 so piercer 76, and particularly piercing section 54, is prevented from moving laterally relative to the axis of guide channel 30.

With further advancement of piercer 76 through guide 68 in guide channel 30, piercing tip 56 advances towards the surface of the eye. When stem section 52 is 3.8 mm inside proximal section 72 of guide channel 30, piercing tip 56 makes contact with and pierces the surface of the eye to make an incision in the sclera.

The advancement of piercing tip 56 and the depth of the incision is monitored with the help of the UBM imaging modality until piercing tip 56 passes through the retina and the retinal pigment epithelium to make an incision to the subretinal space. Due to the triangular shape of piercing section 54 of piercer 76, the distal end of the incision is narrower than the proximal end of the incision.

The depth of the subretinal space in a human eye from the eye surface (and consequently from eye-contacting surface 22) is between 1 mm (X in FIG. 2C) and 1.5 mm (Y in FIG. 2C).

When stem section 52 is about 8 mm inside proximal section 72 of guide channel 30, piercing tip 56 is about 1 mm below eye-contacting surface 22 (X in FIG. 2C).

When stem section 52 is entirely inside (10 mm) proximal section 72 of guide channel 30, piercing tip 56 is about 1.5 mm below eye-contacting surface 22 (Y in FIG. 2C).

As proximal section 72 of guide channel 30 is 10 mm long, piercing tip 56 can penetrate not more than about 1.5 mm below eye-contacting surface 22.

When the incision is made to the subretinal space, the operator withdraws piercer 76 from guide 68.

An injector, analogous to injector 16, but with dimensions appropriate for use with guide 68, is charged with a therapeutic composition and then inserted through guide channel 30 of guide 68 coaxially into the incision to a depth where resistance is felt, indicating contact with a portion of the incision that has substantially the same or a narrower cross sectional size than of the distal tip of the injector. The operator uses the injector in the usual way to inject a therapeutic composition. The composition passes into the sub retinal space.

In accordance with the teachings herein, the injection of the composition leads to a relatively homogenous distribution of the composition in a large portion of the subretinal space of the eye, including to the macula.

In some embodiments, a guide as described herein includes one or more barbs that assists in positioning the guide against a contacted eye. In some such embodiments, such a barb protrudes from the eye-contacting surface and is configured to pierce an eye when the guide is held against an eye to a depth, typically to a depth of less than 1 mm. In some embodiments, a barb is positioned at an angle substantially similar to the angle of the guide channel. In some embodiments, such a barb is flat. In some embodiments, such a barb is curved.

An embodiment of a guide including a barb, guide 78, is schematically depicted in side-cross section in FIG. 3. Guide 78 is substantially identical to guide 68 discussed with reference to FIG. 2, but includes a barb 80 protruding from the bottom of eye-contacting surface 22 in proximity of the distal end of guide channel 30. Barb 80 is a flat 0.2 mm thick triangular blade of surgical stainless steel that is embedded in guide 78 to constitute an extension of guide channel 30. Specifically, barb 80 protrudes 1.8 mm and is angled parallel to guide channel 30 (15° relative to eye contacting surface 22). When guide 78 is placed against an eye so that eye-contacting surface 22 contacts the eye, barb 80 pierces the sclera to a depth of about 0.5 mm, assisting a user in properly placing guide 78 against an eye.

Embodiments of the invention have been described herein primarily with reference to treatment of living human subjects. It is understood, however, that embodiments of the invention are performed for the veterinary treatment of a non-human mammal, such as pigs, dogs, cats, horses, monkeys and bovines.

Embodiments of the invention have been described herein primarily with reference to treatment of living subjects. It is understood that application of the invention for training and educational purposes (as opposed to treating a condition) falls within the scope of the claims, whether on a living non-human subject or on a dead subject, whether on a simulated human body, a human cadaver or on a non-human body, whether on a eye isolated (at least partially) from a body, or on a body.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A device suitable for delivering a therapeutic composition to an eye of a subject, comprising:
   a guide comprising an eye-contacting surface configured to make contact with a surface of said eye for fixing a relative position of said guide to the eye, said guide having a proximal end, a distal end and a guide channel opened at said guide distal end;
   a piercer configured to be inserted through said guide channel and to emerge axially with a distal end of said piercer extending to make an incision in a sclera of said eye without piercing the sensory retina, when said eye-contacting surface is in contact with an anterior portion of said eye near a target location for making said incision; and
   an injector configured to be inserted through said guide channel and to emerge axially with a distal tip of said injector, for injecting said therapeutic composition via said distal tip of said injector into said incision made by said piercer;
   wherein said guide comprises a retainer for retaining said piercer when making said incision and for retaining said injector when injecting said therapeutic composition, and wherein said retainer prevents said distal tip of said injector from extending into said incision further than said retainer permits said piercer to extend when said piercer is inserted into said guide for making said incision.

2. The device of claim 1 provided as a kit, wherein at least one of said guide, said piercer, and said injector is physically separated from the other two.

3. The device of claim 1, wherein said distal end of said piercer is flat and configured to make said incision in a form of a slit.

4. The device of claim 1, wherein said distal end of said piercer comprises a blade.

5. The device of claim 1, wherein said distal tip of said injector having cross-sectional dimensions not smaller than a distal end of said incision made by said piercer in said sclera.

6. The device of claim 1, wherein said distal tip of said injector having cross-sectional dimensions greater than of a distal end of said incision made by said piercer in said sclera.

7. The device of claim 1, wherein said distal tip of said injector is blunt.

8. The device of claim 1, wherein said guide includes at least one barb, said at least one barb protruding from said eye-contacting surface as an extension of said guide channel, and configured for piercing said eye when said guide is placed against said eye, and for said fixing said relative position of said guide to said eye.

9. A method for delivering a therapeutic composition to an eye of a subject, the method comprising:
   inserting a piercer into an anterior portion of said eye and pushing said piercer distally through a thickness of a sclera of said eye, thereby forming an incision in said sclera without piercing a sensory retina of said eye;
   inserting a distal tip of an injector into said sclera and contacting said sclera within said incision, said injector extending no further into said incision than said piercer extended; and
   injecting said therapeutic composition into said incision.

10. The method of claim 9, wherein said piercer is inserted into said eye at an acute angle relative to a surface of said eye, such that said piercer extends at said acute angle 6 mm or less from said surface of said eye in said sclera up to reaching a predetermined depth of 1.5 mm or less from said surface of said eye.

11. The method of claim 10, wherein said angle is not more than about 20°.

12. The method of claim 9, further comprising partially flattening said eye near a target location of said incision.

13. The method of claim 9, wherein said incision is in a form of a slit.

14. The method of claim 9, wherein said distal tip of said injector having cross-sectional dimensions not smaller than a diameter of said distal end of said incision.

15. The method of claim 14, wherein said distal tip of said injector having cross-sectional dimensions greater than a diameter of said distal end of said incision.

16. The method of claim 15, wherein a proximal end of said incision is larger in diameter than said distal end of said incision, and wherein during said step of inserting said injector, said injector distal tip is advanced in said incision to no further than where said injector distal tip cross-sectional dimensions are greater than said incision.

17. The method of claim 9, wherein said step of inserting said piercer and said step of inserting said injector further comprising:

positioning a guide over said eye such that an eye-contacting surface of said guide is in contact with said anterior portion of said eye, said guide having a proximal end, a distal end, and a guide channel opened at said distal end of said guide;

inserting said piercer through said guide channel to assist in making said incision; and inserting said injector through said guide channel to assist in ensuring that said injector is inserted into said incision.

18. The method of claim 9, wherein said incision passes to a subretinal space of said eye.

19. The method of claim 9, wherein said piercer is withdrawn from said incision prior to said step of inserting of said injector.

20. The method of claim 9, wherein said injector is inserted into said incision while said piercer is inside said incision.

21. The method of claim 9, wherein said distal tip of said injector is blunt.

22. The method of claim 9, wherein during said step of inserting said distal tip of said injector into said incision, said distal tip of said injector is advanced only partially into said incision so that said distal tip of said injector is located inside said sclera when said therapeutic composition is injected.

23. The method of claim 9, wherein said step of injecting delivers said therapeutic composition into a subretinal space of said eye via said incision, when said distal tip of said injector is advanced only partially in said incision, for allowing said sclera to seal around a portion of said injector provided in said incision, thereby facilitating a homogenous distribution of said injected therapeutic composition in said subretinal space.

\* \* \* \* \*